US00PP18534P2

(12) United States Plant Patent
Friday

(10) Patent No.: US PP18,534 P2
(45) Date of Patent: Feb. 26, 2008

(54) PEACH TREE NAMED 'P.F. 8 BALL'

(50) Latin Name: *Prunus persica*
Varietal Denomination: P.F. 8 Ball

(76) Inventor: Paul Jan Friday, P.O. Box 850, Coloma, MI (US) 49038

( * ) Notice: Subject to any disclaimer, the term of this patent is extended or adjusted under 35 U.S.C. 154(b) by 184 days.

(21) Appl. No.: 11/344,570

(22) Filed: Feb. 1, 2006

(51) Int. Cl.
*A01H 5/00* (2006.01)

(52) U.S. Cl. ..... Plt./196

(58) Field of Classification Search ..... Plt./196
See application file for complete search history.

*Primary Examiner*—Wendy Haas

(57) ABSTRACT

A new and distinct variety of peach, *Prunus persica,* tree having the following unique combination of desirable features.

1. The new and distinct variety of peach tree is of spreading growth being a regular and productive bearer of large peaches having an average diameter of about 2¾".
2. Producing a very firm fruit having a resilient flesh texture.
3. Blossoms are non-showy when in full bloom.
4. A substantially spherical fruit with skin of dark red color overlying yellow at maturity
5. An early season maturing fruit of good taste, and freestone.
6. An early season maturing fruit of good storage and shelf life.

1 Drawing Sheet

Botanical classification: *Prunus persica.*

ORIGIN OF VARIETY

The new peach tree {hereinafter referred to as the 'P.F. 8 Ball'} was originated by Paul Friday in the experiment orchard, which is maintained for the purposes of breeding peach trees in Coloma, Mich. Coloma is located in the southwest section of Michigan, USDA Hardiness Zone 6A, with observed temperature ranges of minus 12 degree Fahrenheit to 90 degree Fahrenheit, also with annual rainfall of about 40 inches.

In an ongoing mass selection breeding program, superior seedlings of unrecorded parentage are maintained as seed sources for the production of seeds which are collected and planted in mass. The seed producing parent trees are maintained solely as proprietary trees for breeding purposes and have not been released from the experimental orchard, where such trees can be evaluated for there adaptability to local and regional growing conditions. Seeds resulting from open pollination of the trees in the experimental orchard are regularly planted in mass to produce new populations of seedlings, which are cultured and monitored to maturity. Trees with superior attributes are retained for further observation and testing, and contribute seeds to advancing generations of new populations of seedlings.

The tree of this application, 'P.F. 8 Ball', was a single plant from one such a seedling population, and was based on the numerous superior genetic attributes of this tree which are described in the botanical description to follow. While not comprehensive, the details of the botanical description to follow are believed to be a reasonably complete botanical description of the tree of this disclosure.

ASEXUAL REPRODUCTION OF THE VARIETY

The new and distinct variety of peach tree was asexually propagated by budding as performed in an experimental orchard located in Coloma, Mich. The asexual propagation demonstrates that such reproduction of the characteristics of the tree are consistent and are established and transmitted through succeeding propagation.

SUMMARY OF THE VARIETY

The new and very distinct variety of peach tree is of moderate spreading growth and a regular and productive bearer of peaches. A distinct characteristic of the 'P.F. 8 Ball' peach tree is its long internodes, another notable characteristic is it's limb growth pattern producing many natural right angle crotches. The blossoms are characterized by being contracted or partially spread when in full bloom. At the same time petals of the blossoms are of lesser length than the length of petals of normal showy blossom as exemplified by the 'Loring' (non-patented) peach blossom.

The blossoms of the present peach tree at full bloom may be characterized as being non-showy.

Leaf glands are particularly small and insignificant.

The fruit at maturity is large, having flesh that is firm and a light white with no red around the pit.

The skin is smooth having moderate down and is of dark red color overlying dark yellow. At maturity the peach is spherical having an average diameter ranging between about 2½" to 3".

The fruit has a firm flesh and may be described as resilient to the extent that the flesh is yieldable and restorable to its original state when subjected to impact forces, which may cause permanent deformities in peaches of commercial varieties. The firmness of the fruit facilitates handling and packaging of the peaches without damaging the same for shipment. This results in less spoilage and also increases the shelf life.

The fruit matures in the early part of the peach growing season in southwestern Michigan. The fruit as mentioned heretofore is of dark red color overlying dark yellow and has a very attractive appearance.

BRIEF DESCRIPTION OF THE PHOTOGRAPHS

In the accompanying drawing, the top photograph shows the leaves of the plant, depicting upper and lower sides. A tape measure is included showing the length of a leaf.

The bottom photograph shows two (2) whole fruit with one bisected across the axis showing the extent of the light white flesh with no red around the pit. A tape measure is included to show the good size of this fruit.

DESCRIPTION OF VARIETY

The detailed botanical description of the foliage and fruit of the new variety of peach tree is based upon observations of the specimens grown at Coloma, Mich. with the color terminology, other than the terminology expressed in common terms, in accordance with the Pantone Matching System {PMS} as used internationally to identify printed colors.

Botanical classification: *Prunus persica* cultivar 'P.F. 8 Ball'.

Tree:
- *Age.*—Eight (8) years.
- *Height.*—Unpruned 10'.
- *Width.*—Unpruned 10½'.
- *Size.*—Medium.
- *Vigor.*—Medium vigor.
- *Density.*—Medium.
- *Form.*—Spreading.
- *Production.*—Good.
- *Bearer.*—Regular.
- *Disease resistance to bacterial leaf and fruit spot.*—Very resistant.
- *Rootstock.*—Grown in its own roots.

Trunk:
- *Bark.*—Gray (402).
- *Size.*—Medium.
- *Surface.*—Rough.
- *Diameter.*—3½" diameter — 16" above ground at 8 years of age.
- *Lenticels.*—Smooth.
- *Lenticels color.*—Pantone # 406.
- *Lenticels size.*—⅛" to 3/16".

Branches:
- *Size.*—Medium 2" diameter 6" from trunk.
- *Surface.*—Semi-smooth.
- *Lenticels per square inch.*—Seven (7).
- *Lenticels color.*—Pantone #413.
- *Lenticels size.*—⅛" to 3/16".
- *Crotch angles.*—Natural right angles.
- *Branch color.*—Gray (402).
- *Internode length.*—1¼".

Leaves:
- *Size.*—Average length 6" average with 1½".
- *Form.*—Lanceolate. — pointed.
- *Thickness.*—Medium.
- *Texture.*—Glabrous.
- *Margin.*—Serrated.
- *Leaf base shape.*—Acute.
- *Leaf apex shape.*—Pointed.
- *Petiole length.*—⅜".
- *Gland.*—1 on each side of the petiole, glands particularly small and insignificant.
- *Gland shape.*—Flat, very shallow, small.
- *Gland color.*—White.
- *Leaf color.*—Adaxial (Top) or upper leaf surface — green (343).
- *Leaf color.*—Abaxial (Bottom) or bottom leaf surface — green (378).

Flower buds:
- *Size.*—⅜" long— 3/16" wide.
- *Bud shape.*—Ovate.
- *Bud color.*—Pantone # 201.

Flowers:
- *Blooming period.*—Apr. 15, 2005 to Apr. 23, 2005.
- *Bloom size.*—¾" diameter.
- *Bloom depth.*—⅜" deep.
- *Size of petals.*—7/16" long —3/16 wide.
- *Shape of petals.*—Ovate.
- *Petal margins.*—Entire (smooth).
- *Petal base shape.*—Pointed.
- *Petal apex shape.*—Ovate.
- *Petal color.*—Top Pantone #203, bottom Pantone # 217.
- *Petal size.*—7/16" long, 3/16" wide.
- *Number of petals.*—Five (5).
- *Sepal size.*—¼" long—⅛" wide.
- *Sepal shape.*—Ovate.
- *Sepal apex.*—pointed.
- *Sepal base.*—Flat.
- *Sepal color.*—Pantone # 383 with a very little stripe of Pantone # 186 in center.
- *Number of sepals.*—Five (5).
- *Number of anthers.*—22.
- *Anther color.*—Pantone # 145.
- *Number of stamens.*—22.
- *Stamen length.*—3/16".
- *Stamen color.*—Pantone # 206.
- *Pistil length.*—½".
- *Pistil color.*—Pantone # 115.
- *Pollen.*—Present.
- *Flower color.*—Pink (Pantone # 203).
- *Number flowers per cluster.*—2.
- *Fragrance.*—None.

Fruit:
- *Maturity when described.*—Firm ripe.
- *Date of first picking.*—Jul. 25, 2005.
- *Date of last picking.*—Jul. 29, 2005.
- *Size.*—Average 2¾".
- *Form.*—Spherical.
- *Suture.*—Pronounced.
- *Weight.*—6.9 oz.

Skin:
- *Thickness.*—Medium as compared to the species.
- *Texture.*—Medium as compared to the species.
- *Tendency to crack.*—None.
- *Down.*—Light (short as compared to the species).
- *Color.*—About 90% red (Pantone # 202) over dark yellow (Pantone # 148).

Flesh:
- *Texture.*—Firm, non-melting free of fiber.
- *Ripens.*—Evenly.
- *Flavor.*—Very good.
- *Aroma.*—Pleasant, mild.
- *Eating quality.*—Excellent.
- *Brix.*—Average of 13%.
- *Color.*—Light white yellow Pantone # 127.
- *Pit cavity color.*—Pantone # 110.

Stone:
- *Type.*—Freestone.
- *Size.*—1 13/16" long—1¼" wide—1 3/16" thick.
- *Form.*—Ovate.

*Base.*—Straight.
*Apex.*—Pointed.
*Sides.*—Nearly equal.
*Surface.*—Furrowed.
*Color.*—Reddish brown (Pantone # 168).
*Tendency to crack.*—None.
*Kernel.*—13/16"long— 9/16"wide— 3/16"thick.
*Kernel taste.*—Bitterness.
Use: Desert.
Shipping quality: Very good.
Keeping quality: Very good (up to three (3) weeks).
Disease resistance: The fruit is resistance to brown rot.

The tree and its fruit herein described may vary slight as a result of differences in climatic or soil conditions or cultural practices under which the tree may be grown. It is to be understood that the description of the new variety as set forth herein is that of the tree grown under the ecological conditions prevailing at Coloma, Mich.

What is claimed is:

1. A new and distinct variety of peach tree substantially as herein illustrated and described.

* * * * *

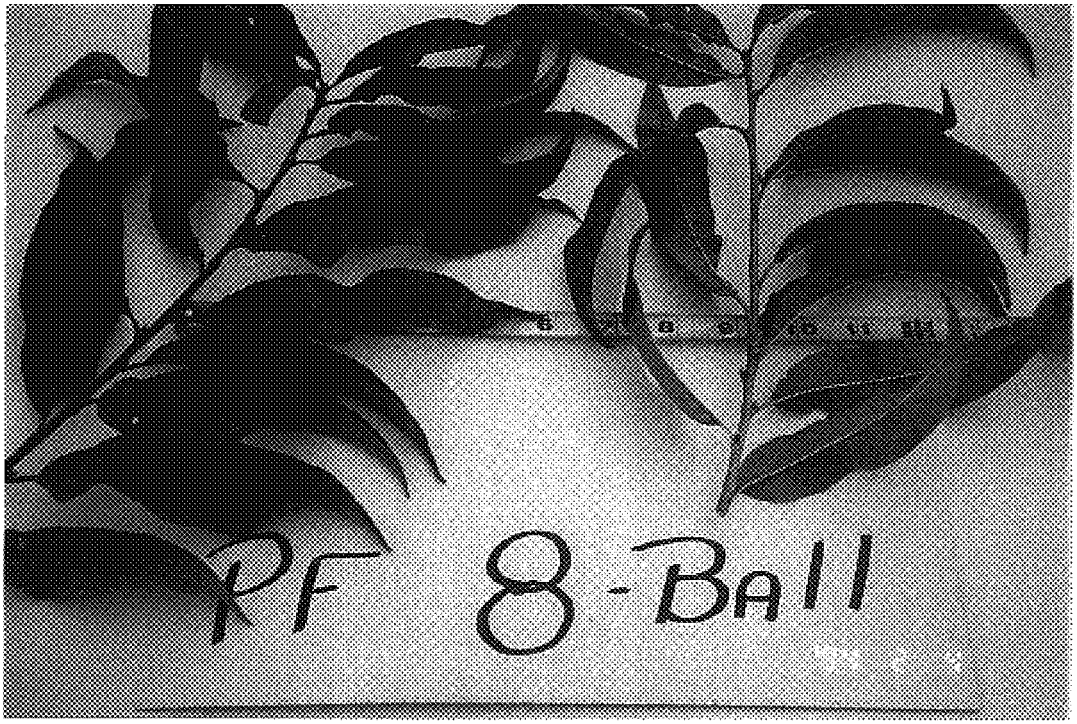
PF 8-Ball
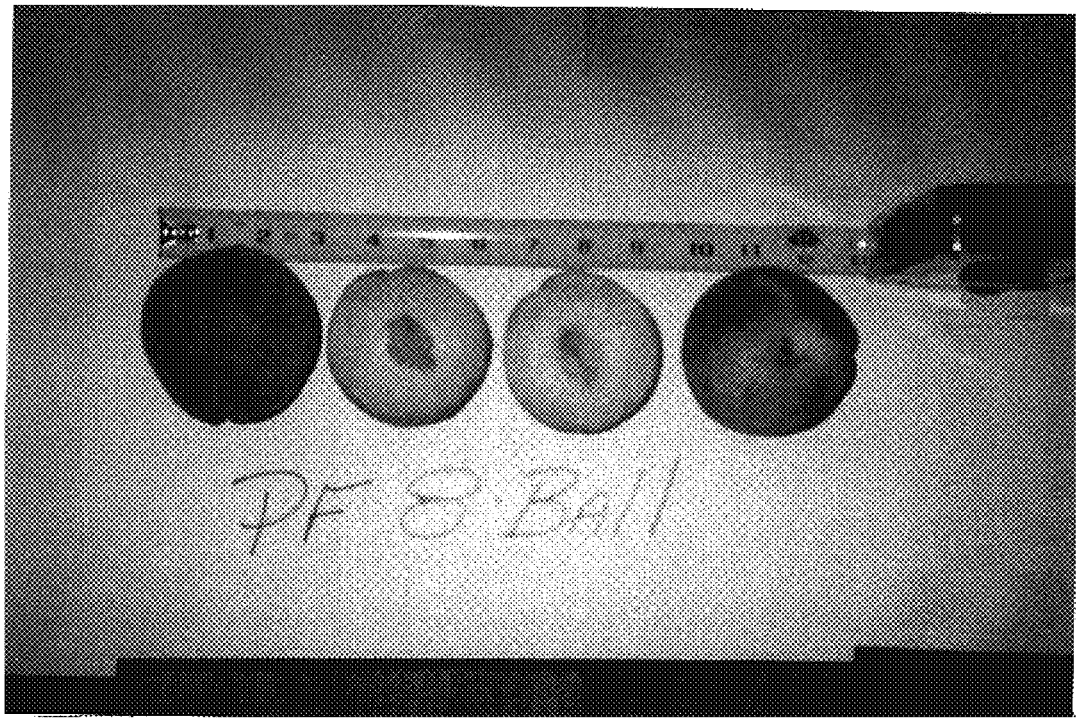
PF 8-Ball